(12) United States Patent
Ahlgren et al.

(10) Patent No.: US 9,339,478 B2
(45) Date of Patent: May 17, 2016

(54) PHARMACEUTICAL FORMULATION

(75) Inventors: Nils Ahlgren, Parsippany, NJ (US); Mark Nuttall, Parsippany, NJ (US); Jeannie Wong, Parsippany, NJ (US); Venkatesh Balasubramanian, Parsippany, NJ (US); Craig Belongie, Parsippany, NJ (US); Ashfaq Khan, Parsippany, NJ (US); Neil Campbell Muir, Hull (GB)

(73) Assignee: RECKITT BENCKISER LLC, Parsippany, NJ (US)

( * ) Notice: Subject to any disclaimer, the term of this patent is extended or adjusted under 35 U.S.C. 154(b) by 0 days.

(21) Appl. No.: 13/021,240

(22) Filed: Feb. 4, 2011

(65) Prior Publication Data

US 2012/0201887 A1 Aug. 9, 2012

(51) Int. Cl.
| | |
|---|---|
| *A61K 9/24* | (2006.01) |
| *A61K 31/09* | (2006.01) |
| *A61K 9/20* | (2006.01) |
| *A61K 9/50* | (2006.01) |
| *A61K 31/137* | (2006.01) |
| *A61K 31/485* | (2006.01) |
| *A61K 45/06* | (2006.01) |

(52) U.S. Cl.
CPC . *A61K 31/09* (2013.01); *A61K 9/20* (2013.01); *A61K 9/209* (2013.01); *A61K 9/2027* (2013.01); *A61K 9/2054* (2013.01); *A61K 9/5047* (2013.01); *A61K 31/137* (2013.01); *A61K 31/485* (2013.01); *A61K 45/06* (2013.01)

(58) Field of Classification Search
CPC ...... A61K 2300/00; A61K 9/20; A61K 9/209
See application file for complete search history.

(56) References Cited

U.S. PATENT DOCUMENTS

| 6,001,392 A | 12/1999 | Wen | |
|---|---|---|---|
| 2003/0049318 A1 | 3/2003 | Davis | |
| 2003/0215508 A1 * | 11/2003 | Davis et al. | 424/468 |
| 2005/0095288 A1 | 5/2005 | Honea | |
| 2008/0008772 A1 * | 1/2008 | Giordano et al. | 424/725.1 |
| 2009/0011027 A1 * | 1/2009 | Pathak et al. | 424/486 |

FOREIGN PATENT DOCUMENTS

| WO | 0182895 A2 | 11/2001 |
|---|---|---|
| WO | 03088952 A1 | 10/2003 |

OTHER PUBLICATIONS

International Preliminary Report on Patentability prepared by Athina Nickitas-Etienne mailed Aug. 15, 2013 for priority application PCT/GB2012/050220.

* cited by examiner

*Primary Examiner* — Dennis J Parad
(74) *Attorney, Agent, or Firm* — Troutman Sanders LLP; Ryan A. Schneider; Troy S. Kleckley

(57) ABSTRACT

A pharmaceutical composition in the form of a tablet including a first portion and a second portion, wherein said first portion includes guaifenesin having an immediate release profile and a second drug having a sustained release profile, and wherein the second portion includes guaifenesin having a sustained release profile. The second drug can be in the form of a drug-resin complex. The second drug can be either an anti-tussive or a decongestant. The drug-resin complex includes a drug complexed to an ion exchange resin. The ion exchange resin can be a polystyrene sulfonate resin, polacrilex resin, polacrilin potassium, cholestyramine resin, or a colestyramine resin. The drug-resin complex can be provided with a coating, the coating thickness being selected to obtain the desired release profile. The drug-resin complex can be provided with a coating level of from 5% to 50%. The coating level can be from 10% to 35%.

31 Claims, 1 Drawing Sheet

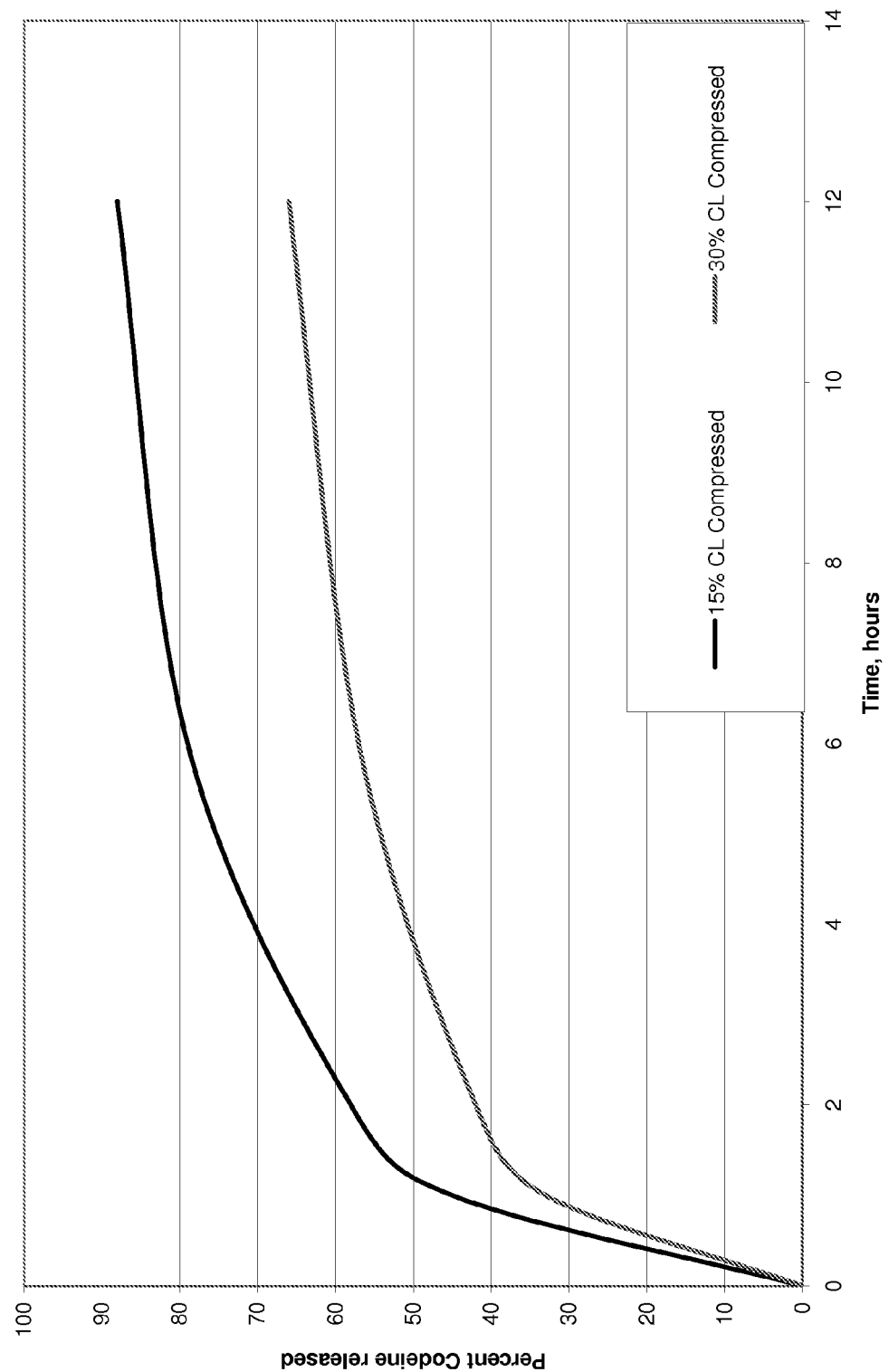

PHARMACEUTICAL FORMULATION

BACKGROUND OF THE INVENTION

1. Field of the Invention

The present invention is directed to a novel pharmaceutical composition comprising guaifenesin and a second drug. In particular, the present application is directed to a novel pharmaceutical composition comprising guaifenesin and a second drug which is an antitussive or a decongestant. More particularly, the present application is directed to a composition comprising guaifenesin having both immediate and extended release profiles and codeine having an immediate release profile.

2. Description of Related Art

Compounds such as codeine are known to have both antitussive and pain relieving properties. The antitussive effect occurs at a lower dose than that needed to provide pain relief.

In addition, compounds such as codeine are used in combination with compounds that treat other symptoms of a cough/cold or flu, e.g. expectorants, mucus thinning drugs, decongestants and/or antihistamines. However, a dose of an antitussive compound such as codeine typically provides a therapeutic effect for about 2.5-3 hours, whereas many of the compounds often used with this type of antitussive compound provide therapeutically effective plasma concentrations per dose over a period that is significantly different. For example, a dose of an expectorant such as guaifenesin will usually provide relief for about one hour, and decongestants usually provide relief for about 4 to 8 hours.

As a result, there is little benefit to be gained in combining an antitussive such as codeine with a drug having a shorter or longer therapeutically effective period in a single dosage form. In such a combination, one drug (e.g. codeine) may still provide the desired effect when the other drug has already ceased to be effective, or the other drug may continue to exert its effect, which would prevent administration of a further dose of the antitussive.

It would be desirable if patients suffering from a cough/cold/flu-type conditions, which an antitussive like codeine would provide relief against could be combined with a different drug, such as guaifenesin, in order to obtain relief from symptoms that the antitussive does not treat.

Sustained release pharmaceutical formulations provide a significant advantage over immediate release formulations to both clinicians and their patients. Sustained release dosage forms provide for fewer daily dose administrations than their immediate release counterparts. For example, a standard dosage regimen for a 400 mg immediate release drug with a short half-life, such as guaifenesin, requires administration three times within twelve hours to maintain adequate bioavailability to achieve the desired therapeutic effect.

Besides reducing the frequency of dosing and providing a more consistent therapeutic effect, sustained release dosage forms generally help reduce side effects caused by a drug. Because sustained release dosage forms deliver the drug in slow, incremental amounts versus the cyclic high and low concentrations of immediate release formulations, it is easier for a patient's body to digest the drug, thereby avoiding undesirable side-effects. For patients who self-administer therapies, sustained release dosage forms generally result in greater compliance due to the lower frequency of dosing, lower quantity of dosage units to be consumed, and reduced undesired side-effects.

Generally, sustained release formulations contain drug particles mixed with or covered by a polymer material, or blend of materials, which is resistant to degradation or disintegration in the stomach and/or in the intestine for a selected period of time. Release of the drug may occur by leeching, erosion, rupture, diffusion or similar actions depending upon the nature of the polymer material or polymer blend used.

Furthermore, most formulations that claim twelve hour potency release almost all of their drug within six to eight hours, making the formulation less therapeutically effective towards the end of the twelve hour period. To prevent blood serum concentrations of drug from falling below a therapeutically effective level (Cmin) at extended time periods, many manufacturers increase the drug strength of the dosage form. The increase in drug strength, however, results in a concomitant increase in side-effects.

Other pharmaceutical manufacturers have made tablets and capsules containing a combination of an immediate release formulation and a sustained release formulation to improve the release profile of certain sustained release dosage forms. Although this solution improves the Cmax and length of time before the drug appears in the blood stream in some formulations, the extended therapeutic effect is not improved.

Furthermore, medicaments have different solubility properties and pH dependencies, which affect dissolution rate and bioavailability. Bioavailability can also be affected by a number of factors such as the amounts and types of adjuvants used, the granulation process, compression forces (in tablet manufacturing), surface area available for dissolution and environmental factors such as agitation in the stomach and the presence or absence of food. Due to these numerous factors, specific formulations play an important role in the preparation of prolonged action solid dosage forms, particularly in the preparation of solid dosage forms that achieve appropriate bioavailability for optimum therapeutic effect.

WO 01/082895 discloses a composition which comprises immediate and sustained release portions, both of which contain guaifenesin. WO 03/088952 discloses a composition which also comprises guaifenesin-containing immediate and sustained release. The specification exemplifies compositions which also include dextromethorphan or pseudoephedrine.

BRIEF SUMMARY OF THE INVENTION

Briefly described, in a preferred form, the present invention provides a pharmaceutical composition in the form of a tablet comprising a first portion and a second portion wherein said first portion comprises guaifenesin having an immediate release profile and a second drug having a sustained release profile and wherein said second portion comprises guaifenesin having a sustained release profile.

Typically the second drug is in the form of a drug-resin complex. The second drug can be either an anti-tussive or a decongestant. Typically, the second drug can be selected from codeine, pseudoephedrine, phenylephrine, dextromethorphan and hydrocodone. Preferably the second drug is codeine The drug-resin complex comprises a drug complexed to an ion exchange resin. The ion exchange resin can be a polystyrene sulfonate resin, polacrilex resin, polacrilin potassium, cholestyramine resin, or a colestyramine resin. A preferred resin is a sodium polystyrene sulfonate resin.

The drug-resin complex can be provided with a coating, the coating thickness being selected to obtain the desired release profile. The drug-resin complex can be provided with a coating level of from 5% to 50%. The coating level can be from 10% to 35%.

The term 'coating level' indicates the weight proportion of the coated drug-resin complex that is the coating itself, for example a coating level of 15% indicates that 15% of the overall weight of the drug-resin complex is the coating layer.

In one preferred embodiment the drug resin complex having a coating level of 30% has the following dissolution profile in USP apparatus 1 (baskets) at 50 rpm in 0.1N HCl at 37° C.:

| Time (hours) | Average % Codeine released |
| --- | --- |
| 1 | 18-48 |
| 2 | 27-57 |
| 6 | 42-72 |
| 12 | 51-81 |

In a particularly preferred embodiment the drug resin complex having a coating level of 30% has the following dissolution profile in USP apparatus 1 (baskets) at 50 rpm in 0.1N HCl at 37° C.:

| Time (hours) | Average % Codeine released |
| --- | --- |
| 1 | 33 |
| 2 | 42 |
| 6 | 57 |
| 12 | 66 |

In an alternative preferred embodiment the drug resin complex having a coating of 15% has the following dissolution profile in USP apparatus 1 (baskets) at 50 rpm in 0.1N HCl at 37° C.:

| Time (hours) | Average % Codeine released |
| --- | --- |
| 1 | 30-60 |
| 2 | 43-73 |
| 6 | 64-94 |
| 12 | at least 73 |

In a particularly preferred embodiment the drug-resin complex having a coating level of 15% has the following dissolution profile in USP apparatus 1 (baskets) at 50 rpm in 0.1N HCl at 37° C.:

| Time (hours) | Average % Codeine released |
| --- | --- |
| 1 | 45 |
| 2 | 58 |
| 6 | 79 |
| 12 | 88 |

Alternatively the drug-resin complex is uncoated.

The said second drug can also be the sustained release portion.

The portion having the sustained release guaifenesin can comprise a release-delaying matrix comprising a hydrophilic polymer and a water-insoluble polymer.

The release-delaying matrix can comprise hydrophilic polymer and water-insoluble polymer in a weight ratio selected from 1:1 to 9:1, from 3:2 to 6:1, or from 2:1 to 4:1.

The total amount of guaifenesin can be between 500 mg and 1300 mg, preferably from 600 mg to 1200 mg. In a preferred embodiment the formulation contains 1200 mg of guaifenesin. In an alternative preferred embodiment the formulation contains 600 mg of guaifenesin.

The total amount of the second drug can be up to 100 mg, preferably 20-80 mg. In a preferred embodiment the composition contains an amount of codeine that is therapeutically equivalent to 60 mg of codeine phosphate. In an alternative preferred embodiment the composition contains an amount of codeine that is therapeutically equivalent to 30 mg of codeine phosphate.

In a preferred embodiment the composition comprises 1200 mg of guaifenesin and an amount of codeine that is therapeutically equivalent to 60 mg of codeine phosphate. In an alternative preferred embodiment the composition comprises 600 mg of guaifenesin and an amount of codeine that is therapeutically equivalent to 30 mg of codeine phosphate.

The immediate release portion comprises microcrystalline cellulose, crospovidone and magnesium stearate.

Typically the second drug is codeine and the ratio of the total quantity of guaifenesin to codeine in the same portion is from 1:1 to 30:1; preferably from 1:1 to 25:1, by weight.

The ratio of the immediate release quantity of guaifenesin to the sustained release quantity of guaifenesin can be from 1:3 to 1:15, preferably from 2:3 to 1:11, by weight.

Typically, at least 60% of the guaifenesin particles used to make the drug product have a particle size in the range of from 25 μm to 2.0 mm. Typically, the guaifenesin particles have a particle size in the range of from 50 μm to 500 μm.

The formulation can comprise immediate release and sustained release portions each comprising abutting planar layers which form a bi-layer tablet.

The formulation can comprise a capsule that contains discrete or associated immediate release and sustained release portions.

The sustained release portion can be coated by a layer of the immediate release portion.

Each drug in the formulation can exhibit a therapeutic effect for a period of 12 hours.

According to a second aspect of the present invention there is provided the composition of the first aspect for temporary treatment of bronchial mucus accumulation, cough and nasal congestion.

BRIEF DESCRIPTION OF THE DRAWING

The sole FIGURE is a chart of percent codeine released over time, wherein CL Compressed refers to (a) the coating level of the bead (15% or 30%) and (b) that the layer comprising the codeine bead is compressed.

DETAILED DESCRIPTION OF THE PREFERRED EMBODIMENTS

To facilitate an understanding of the principles and features of the various embodiments of the invention, various illustrative embodiments are explained below. Although preferred embodiments of the invention are explained in detail, it is to be understood that other embodiments are contemplated. Accordingly, it is not intended that the invention is limited in its scope to the details of ingredients and arrangement of components set forth in the following description or illustrated in the drawing. The invention is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural references unless the context clearly dictates otherwise. For example, reference to an ingredient is intended also to include composition of a plurality of ingredients. References to a composition containing "a" constituent is intended to include other constituents in addition to the one named.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

Embodiments of the present invention will now be described, by way of example only with reference to the accompanying FIGURE which illustrates the dissolution profiles for the codeine from two drug resin complexes, the first drug-resin complex being coated such that it exhibits a slower release profile than the second drug-resin complex and vice versa.

Coated Codeine Polistirex

| Ingredient | Example 1 (wt %) | Example 2 (wt %) |
|---|---|---|
| Codeine Phosphate | 33.25 | 40.375 |
| Sodium Polystyrene Sulfonate (Amberlite IRP69) | 33.25 | 40.375 |
| Sorbitol 70% solution | 3.50 | 4.25 |
| Ethylcellulose | 25.50 | 12.75 |
| Triethyl Citrate | 4.50 | 2.25 |
| Total | 100.0 | 100.0 |

The codeine resin can be made in the following way. A suspension of codeine and the polystyrene sulfonate resin (Amberlite IRP69) in an aqueous sorbitol solution is stirred for 4-6 hours and then filtered under pressure. The filtered solid is then dried, and screened using a 40 mesh screen. The resulting drug-resin beads are coated with a solution which contains acetone/methanol/ethyl cellulose/triethyl citrate. The resulting coated beads are screened using a 50 mesh screen.

The thickness of the coating used on the resin/active particle is selected to ensure that the desired release profile is achieved.

A tablet of the guaifenesin/codeine resin combination can be made in the following way.

The modified-release portion containing guaifenesin as the only active can be made in a similar way. Guaifenesin, hypromellose (Methocel E10M), carbomer (Carbopol 974), and blue dye are blended for about twenty minutes. Magnesium stearate is then added and blending continued for about another ten minutes to prepare the sustained release formulation.

The resulting tablet has the following amounts of each component:

Layer 1—Immediate Release GGE and MR Codeine Polistirex

| Ingredient | Example 1 (wt % (mg)) | Example 2 (wt % (mg)) |
|---|---|---|
| Guaifenesin | 32.39 (210.5) | 32.39 (210.5) |
| Coated Codeine Polistirex | 30.07 (195.4) | 24.36 (158.3) |
| Microcrystalline Cellulose | 32.04 (208.3) | 37.75 (245.4) |
| Crospovidone | 5.00 (32.50) | 5.00 (32.50) |
| Magnesium Stearate | 0.50 (3.30) | 0.50 (3.30) |
| Total | 100.00 (650.00) | 100.00 (650.00) |

Layer 2—Modified Release GGE

| Ingredient | Example 1 (wt % (mg)) | Example 2 (wt % (mg)) |
|---|---|---|
| Guaifenesin | 95.77 (1052.60) | 95.77 (1052.60) |
| Hypromellose | 2.42 (26.60) | 2.42 (26.60) |
| Carbomer 934P | 1.14 (12.50) | 1.14 (12.50) |
| FD&C Blue | 0.15 (1.60) | 0.15 (1.60) |
| Magnesium Stearate | 0.52 (5.70) | 0.52 (5.70) |
| Total | 100.00 (1099.00) | 100.00 (1099.00) |

Final Tablet

| Ingredient | Example 1 (wt % (mg)) | Example 2 (wt % (mg)) |
|---|---|---|
| Guaifenesin | 72.22 (1263.10) | 72.22 (1263.10) |
| Coated Codeine Polistirex | 11.17 (195.40) | 9.05 (158.30) |
| Hypromellose | 1.52 (26.60) | 1.52 (26.60) |
| Microcrystalline Cellulose | 11.91 (208.30) | 14.03 (245.40) |
| Crospovidone | 1.86 (32.50) | 1.86 (32.50) |
| Carbomer 934P | 0.71 (12.50) | 0.71 (12.50) |
| FD&C Blue | 0.09 (1.60) | 0.09 (1.60) |
| Magnesium Stearate | 0.51 (9.00) | 0.51 (9.00) |
| Total | 100.00 (1749.00) | 100.00 (1749.00) |

An advantage of the present invention is that there is provided a formulation which allows independent controlled release of the second active without impacting the dissolution properties of the guaifenesin.

In addition, the formulation potentially allows for the reduction of observed food effects for drugs that show lipid variability in clinical evaluation and allows protection of actives from compatibility concerns that may lead to stability degradation Further modifications and improvements can be made without departing from the scope of the invention described herein.

We claim:

1. A pharmaceutical composition in the form of a tablet or capsule comprising:
    about 72 wt % guaifenesin;
    about 11% coated codeine polistirex;
    about 1.5% hypromellose;
    about 12% microcrystalline cellulose;
    about 1.9% crospovidone;
    about 0.7% carbomer 934P;
    about 0.09% FD&C Blue; and
    about 0.5% magnesium stearate.

2. The pharmaceutical composition as claimed in claim 1, comprising a first portion and a second portion,
   wherein said first portion comprises guaifenesin having an immediate release profile and a second drug having a sustained release profile;
   wherein said second portion comprises guaifenesin having a sustained release profile;
   wherein the second drug is in the form of a coated polistirex complex, and the second drug is codeine.

3. The pharmaceutical composition as claimed in claim 2, the coated codeine polistirex complex having a thickness to obtain the desired release profile.

4. The pharmaceutical composition as claimed in claim 3, wherein the coated codeine polistirex complex is provided with a coating level of from 5% to 50%.

5. The pharmaceutical composition as claimed in claim 3, wherein the coating level is from 10% to 35%.

6. The pharmaceutical composition as claimed in claim 3, wherein the coated codeine polistirex complex having a coating level of 30% has the following dissolution profile in USP apparatus 1 (baskets) at 50 rpm in 0.1 N HCl at 37° C.:

| Time (hours) | Average % Codeine released |
|---|---|
| 1 | 18-48 |
| 2 | 27-57 |
| 6 | 42-72 |
| 12 | 51-81. |

7. The pharmaceutical composition as claimed in claim 6, wherein the coated codeine polistirex complex having a coating level of 30% has the following dissolution profile in USP apparatus 1 (baskets) at 50 rpm in 0.1 N HCl at 37° C.:

| Time (hours) | Average % Codeine released |
|---|---|
| 1 | 33 |
| 2 | 42 |
| 6 | 57 |
| 12 | 66. |

8. The pharmaceutical composition as claimed in claim 3, wherein the coated codeine polistirex complex having a coating of 15% has the following dissolution profile in USP apparatus 1 (baskets) at 50 rpm in 0.1 N HCl at 37° C.:

| Time (hours) | Average % Codeine released |
|---|---|
| 1 | 30-60 |
| 2 | 43-73 |
| 6 | 64-94 |
| 12 | at least 73. |

9. The pharmaceutical composition as claimed in claim 8, wherein the coated codeine polistirex complex having a coating level of 15% has the following dissolution profile in USP apparatus 1 (baskets) at 50 rpm in 0.1 N HCl at 37° C.:

| Time (hours) | Average % Codeine released |
|---|---|
| 1 | 45 |
| 2 | 58 |
| 6 | 79 |
| 12 | 88 |

10. The pharmaceutical composition as claimed in claim 2, wherein the said second drug is also the sustained release portion.

11. The pharmaceutical composition as claimed in claim 2, wherein the portion having the sustained release guaifenesin comprises a release-delaying matrix comprising a hydrophilic polymer consisting of hypromellose and a water-insoluble polymer consisting of carbomer 934P.

12. The pharmaceutical composition as claimed in claim 11, wherein the release-delaying matrix comprises hydrophilic polymer and water-insoluble polymer in a weight ratio selected from one of the following: from 1:1 to 9:1, from 3:2 to 6:1, or from 2:1 to 4:1.

13. The pharmaceutical composition as claimed in claim 2, wherein the total amount of guaifenesin is between 500 mg and 1300 mg.

14. The pharmaceutical composition as claimed in claim 13, wherein the total amount of guaifenesin is between 600 mg to 1200 mg.

15. The pharmaceutical composition as claimed in claim 13, wherein the formulation contains 1200 mg of guaifenesin.

16. The pharmaceutical composition as claimed in claim 13, wherein the formulation contains 600 mg of guaifenesin.

17. The pharmaceutical composition as claimed in claim 2, wherein the total amount of the second drug can be up to 100 mg.

18. The pharmaceutical composition as claimed in claim 17, wherein the total amount of the second drug is between 20-80 mg.

19. The pharmaceutical composition as claimed in claim 17, wherein the composition contains an amount of codeine that is therapeutically equivalent to 60 mg of codeine phosphate.

20. The pharmaceutical composition as claimed in claim 17, wherein the composition contains an amount of codeine that is therapeutically equivalent to 30 mg of codeine phosphate.

21. The pharmaceutical composition as claimed in claim 2, wherein the composition comprises 600 mg of guaifenesin and an amount of codeine that is therapeutically equivalent to 30 mg of codeine phosphate.

22. The pharmaceutical composition as claimed in claim 2, wherein the immediate release portion comprises microcrystalline cellulose, crospovidone and magnesium stearate.

23. The pharmaceutical composition as claimed in claim 2, the ratio of the total quantity of guaifenesin to codeine in the same portion is selected from one of the following: from 1:1 to 30:1, by weight; or from 1:1 to 25:1, by weight.

24. The pharmaceutical composition as claimed in claim 2, wherein the ratio of the immediate release quantity of guaifenesin to the sustained release quantity of guaifenesin is selected from one of the following: from 1:1 to 1:15, by weight; or from 2:3 to 1:11, by weight.

25. The pharmaceutical composition as claimed in claim 2, wherein at least 60% of the guaifenesin used to make the tablet or capsule have a particle size in the range of from 25 µm to 2.0 mm.

26. The pharmaceutical composition as claimed in claim 2, wherein at least 60 of the guaifenesin used to make the tablet or capsule have a particle size in the range of from 50 µm to 150 µm.

27. The pharmaceutical composition as claimed in claim 1, wherein the formulation comprises immediate release and sustained release portions each comprising abutting planar layers which form a bi-layer tablet.

28. The pharmaceutical composition as claimed in claim 2, wherein the formulation comprises a capsule that contains discrete or associated immediate release and sustained release portions.

29. The pharmaceutical composition as claimed in claim 2, wherein the sustained release portion is coated by a layer of the immediate release portion.

30. The pharmaceutical composition as claimed in claim 2, wherein each drug in the formulation exhibits a therapeutic effect for a period of 12 hours.

31. The pharmaceutical composition as claimed in claim 2 for temporary treatment of bronchial mucus accumulation, cough and nasal congestion.

\* \* \* \* \*